United States Patent [19]
Girijavallabhan et al.

[11] 4,443,373
[45] Apr. 17, 1984

[54] PROCESS FOR THE PRODUCTION OF ANTIBIOTIC PENEMS

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Kenilworth, N.J.

[21] Appl. No.: 363,710

[22] Filed: Mar. 30, 1982

[51] Int. Cl.$^3$ .................. C07D 499/04; C07D 499/00
[52] U.S. Cl. ............................ 260/245.2 R; 424/270; 424/271; 260/239 A
[58] Field of Search .................. 260/245.2 R; 424/270

[56] References Cited

U.S. PATENT DOCUMENTS 4,282,236 8/1981 Broom .......................... 260/245.2 R
4,283,531 8/1981 Ganguly et al. ............. 260/245.2 R

FOREIGN PATENT DOCUMENTS 2074563A 11/1981 United Kingdom .

Primary Examiner—Nicholas S. Rizzo
Attorney, Agent, or Firm—Anita W. Magatti; Gerald S. Rosen

[57] ABSTRACT

There is disclosed a process for preparing 6-hydroxyethyl-2-alkylthio penem-3-carboxylates by a multi-step process comprising reacting an azetidinone having a protected hydroxy group at the 5 position with a diester of ketomalonic acid, chlorinating the resulting N-substituted azetidinone, removing the chlorine and OH protecting group, reacting the resulting compound with a silver salt to form a silver thio substituted at the 4 position of the azetidinone, cyclizing with a thiocarbonyl compound, then reacting the resulting penam with a fluoride to form a penam-penem tautomer, reacting the tautomer with a halide or ethylenically unsaturated compound followed by deprotecting the carboxyl at the 3 position to form the final penem product in high yield.

16 Claims, No Drawings

PROCESS FOR THE PRODUCTION OF ANTIBIOTIC PENEMS

BACKGROUND

This invention relates to a process for preparing 6-hydroxyethyl-2-alkylthio penem-3-carboxylate antibiotics (referred to herein as penems).

Penems are a recent addition to the family of synthetic beta-lactam antibiotics and have been prepared by laborious, time consuming, multistep processes which result in low yields and are thus uneconomical.

There is a need, therefore, for a facile high yield process for preparing penems which is economical.

SUMMARY

The present invention provides a novel, facile process for preparing antibiotic penems using novel intermediates and novel reaction steps. The process of this invention is a multi-step process which nevertheless is easily and economically conducted since many of the intermediates need not be isolated and it results in high yields.

DETAILED DESCRIPTION

The present invention provides a process for the production of penems of the formula:

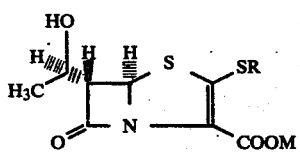

(I)

wherein R is methyl, ethyl, propyl or isopropyl; and M is an alkali metal cation; which comprises:

(a) reaction of an azetidinone of the formula

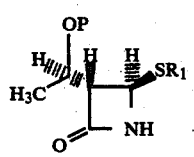

(II)

wherein P is a removable hydroxy protecting group; and $R_1$ is a sulfur protecting group selected from triphenylmethyl; 2-pyranyl, or lower alkyl carbonyl;

with a compound of the formula IIIa and IIIb

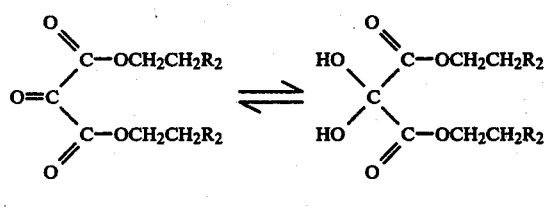

wherein $R_2$ is trimethylsilyl, cyano, t-butyl diphenylsilyl or a sulfone of the formula $-SO_2R^1$ wherein $R^1$ is aryl; to form the intermediate of the formula IV

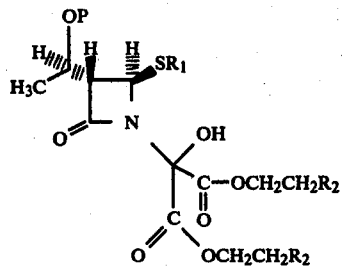

(IV)

wherein P, $R_1$ and $R_2$ are as hereinabove defined;

(b) treatment of the compound of formula IV with a chlorinating agent to form the following compound of formula V

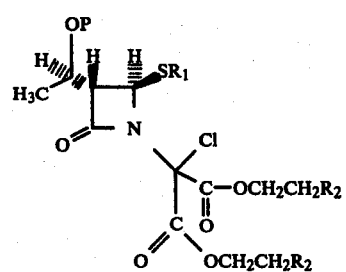

(V)

where P, $R_1$ and $R_2$ are as hereinabove defined;

(c) treatment of the compound of formula V with elemental zinc to effect removal of the chlorine and the removable hydroxy protecting group, and, if a removable hydroxy protecting group is utilized which is not removable with zinc, subsequent removal of said hydroxy protecting group, producing a compound of formula VI

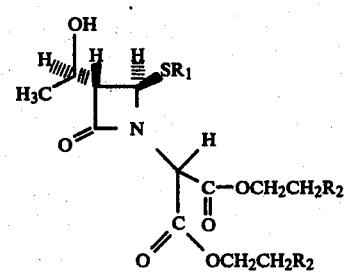

(VI)

where $R_1$ and $R_2$ are as hereinabove defined;

(d) treatment of the compound of formula VI with a reactive silver, copper or mercury salt to form the compound of formula VII

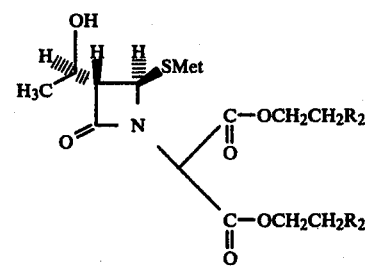

(VII)

wherein $R_2$ is hereinabove defined and Met is silver, copper or mercury;

(e) reaction of the compound of formula VII with a thiocarbonyl compound of formula VIII $$S=C(-Y)_2 \quad \text{(VIII)}$$

wherein Y is a leaving group;
to form a compound of formula IX

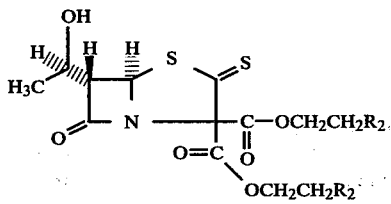

(IX)

wherein $R_2$ is as hereinabove defined;

(f) treatment of the compound of formula IX with one equivalent of fluoride ion to form the tautomeric compound of formulae Xa and Xb

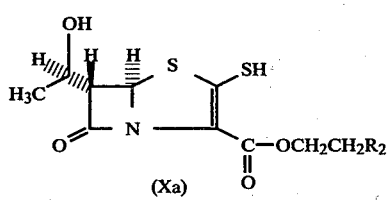

(Xa)

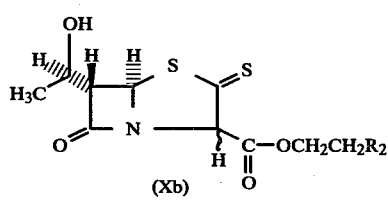

(Xb)

wherein $R_2$ is as hereinabove defined;

(g) reaction of the compound of formulas Xa and Xb with either a compound of the formula XI $$R-Z \quad \text{(XI)}$$

wherein R is as hereinabove defined and Z is a leaving group to make compounds of formula I wherein R is methyl, ethyl, propyl or isopropyl; or a compound of formula XII $$R_3-CH=CH_2 \quad \text{(XII)}$$

wherein $R_3$ is hydrogen or methyl, to make compounds of formula I wherein R is ethyl, propyl or isopropyl; forming a compound of formula XIII

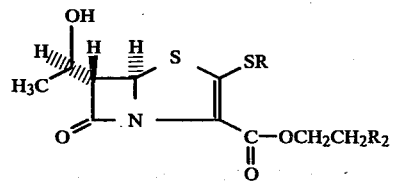

(XIII)

wherein R is methyl, ethyl, propyl or isopropyl and $R_2$ are as hereinabove defined; and (h) treatment of a compound of formula XIII with another equivalent of fluoride ion to form a compound of formula I.

Certain of the intermediate compounds produced while the process of this invention is carried out are novel compounds. Thus, the compounds of formula IV, V, VI, VII, IX, Xa and Xb are novel and constitute a part of this invention. The compound of formulas Xa and Xb exists in two tautomeric forms at equilibrium. This tautomer is of particular importance since it can be utilized to prepare not only the known penems of formula I, but can also be utilized to prepare other penems having structural variations connected to the 2-thio substituent on the penem nucleus. The process for preparing compounds Xa and Xb according to this invention is a facile, high yielding method which enables one to prepare economically, known valuable penems such as (5R,6S,8R)-2-ethylthio-6(1-hydroxyethyl)penem-3-carboxylic acid.

The process according to this invention, for preparing a compound of the formulas Xa and Xb

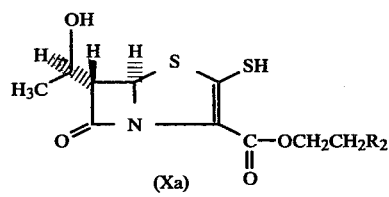

(Xa)

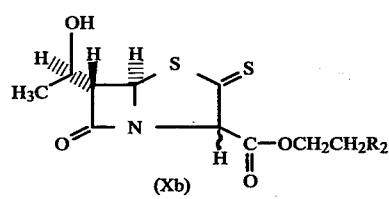

(Xb)

wherein $R_2$ is trimethylsilyl, cyano, t-butyldiphenylsilyl or a sulfone of the formula $-SO_2R^1$ wherein $R_1$ is aryl, comprises (a) reaction of an azetidinone of the formula II

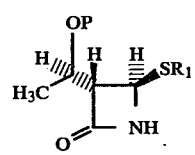

(II)

wherein P is a removable hydroxy protecting group; and $R_1$ is a triphenylmethyl, 2-pyranyl or lower alkyl carbonyl group; with a compound of formulae IIIa and IIIb

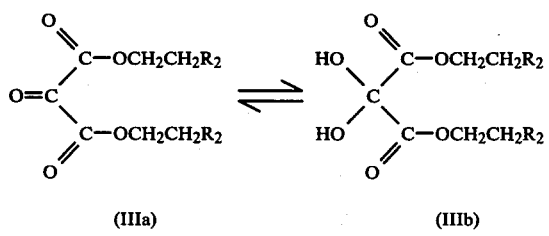

(IIIa)    (IIIb)

wherein $R_2$ is trimethysilyl, cyano, t-butyldiphenylsilyl, or a sulfone of the formula $-SO_2R^1$ wherein $R^1$ is aryl; to form a compound of formula IV

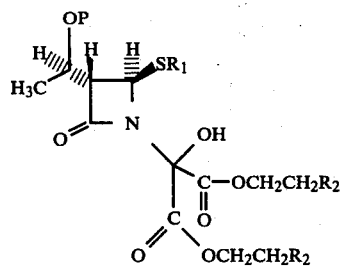

(IV)

wherein P, $R_1$ and $R_2$ are as hereinabove defined;

(b) treatment of a compound of formula IV with a chlorinating agent to form a compound of formula V

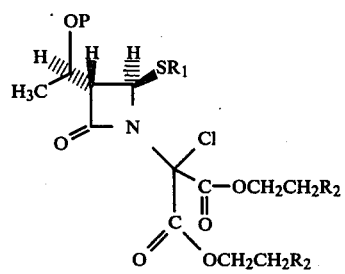

(V)

wherein P, $R_1$ and $R_2$ are as hereinabove defined;

(c) treatment of a compound of formula V with elemental zinc to effect removal of the chlorine and the removable hydroxy protecting group, and, if a removable hydroxy protecting group is utilized which is not removable with zinc, subsequent removal of said hydroxy protecting group, producing a compound of formula VI

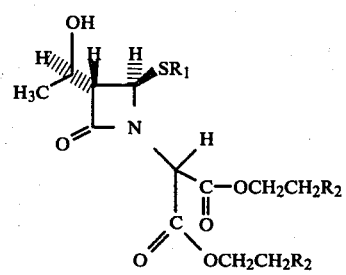

(VI)

wherein $R_1$ and $R_2$ are as hereinabove defined;

(d) treatment of a compound of formula VI with a reactive silver, copper or mercury salt to form a compound of formula VII.

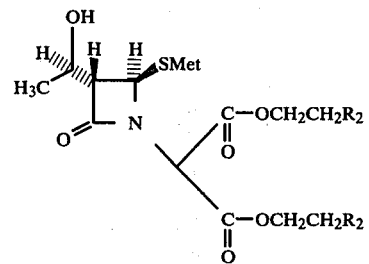

(VII)

wherein $R_2$ is as hereinabove defined and Met is silver, copper or mercury;

(e) reaction of a compound of formula VII with a thiocarbonyl compound of formula VIII

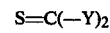

(VIII)

wherein Y is a leaving group; to form a compound of formula IX

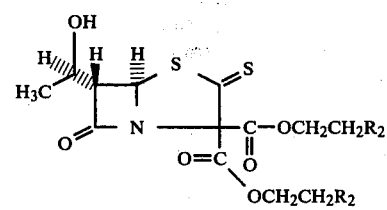

(IX)

wherein $R_2$ is as hereinabove defined; and (f) treatment of a compound of formula IX with one equivalent of fluoride ion to form a compound of formulae Xa and Xb.

As used herein "lower alkyl" means straight and branched chain alkyls of 1 to 6 carbon atoms and are exemplified by methyl, ethyl, isopropyl, propyl, butyl, t-butyl, pentyl, hexyl and the like.

The term "removable hydroxy protecting group" refers to any such group conventionally used for this purpose, with the only requirements being compatability with the hydroxy substituent on the penem and removability utilizing elemental zinc or any other conventional agent for this purpose which will not adversely affect the penem structure. For the purposes of this invention, trichloroethoxy carbonyl is a highly preferred hydroxy protecting group, but others, such as dimethyltributylsilyl and trimethylsilyloxycarbonyl are also utilizable.

The term "lower alkyl carbonyl" refers to a group of the formula

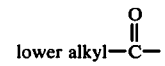

Such groups are typified by acetyl, propionyl, butyryl, and the like.

The term "aryl" as used herein refers to phenyl and phenyl substituted by one or more substituent groups such as chloro, bromo, fluoro, lower alkyl, hydroxy, nitro, amino, aminomethyl, lower monoalkylamino, lower dialkylamino, lower alkoxy and carboxy. Such substituted aryl groups represented by $R_2$ can be, for example, 4-hydroxyphenyl, 3,4-dichlorophenyl, 2,6-dimethoxyphenyl, 4-methylphenyl, 2-fluorophenyl, 4-carboxyphenyl, 3-nitrophenyl, 4-aminophenyl, 3- aminophenyl, 4-dimethylaminophenyl, 4-aminomethylphenyl and 4-ethoxyphenyl.

The term "lower alkoxy" as used herein refers to alkoxy groups which contain 1 to 6 carbon atoms and are exemplified by methoxy, ethoxy, propoxy, and the like.

The preferred sterochemistry of the reactants and intermediates in the instant process is as indicated in the various formulas, i.e. (5R,6S,8R). However, it is to be understood, that the process of this invention is operative for other stereoisomers and involves merely the selection of the starting material of the desired stereochemical configuration.

In a highly preferred embodiment of the present invention, the intermediates formed in each reaction step are not isolated but remain in the reaction vessel and are treated according to the next reaction step. This facilitates the process to a very great extent, since several steps can be carried out in the same solvent, without regard to separation of the desired product. For instance, in a preferred embodiment, the alkyl silyl ester of formula III is added to the intermediate of formula II to form the hydroxy intermediate of formula IV. This intermediate of formula IV is then directly treated with the chlorinating agent, preferably thionyl chloride, to form the chloride intermediate of formula V. This intermediate, again without isolation, is treated directly with elemental zinc to concomitantly remove the hydroxy protecting group on the 6-substituent and the chlorine atoms so as to afford the intermediate of formula VI. Thus, steps (a), (b) and (c) of either of the aforementioned reaction sequences are conducted in the same reaction vessel, in the same solvent, and without any wastage caused by isolation of the intermediate compounds.

Again, in a highly preferred embodiment, the intermediate of formula VII, is utilized directly in the next step without isolation. Thus, steps (d) and (e) are conducted sequentially.

It is likewise preferred to dispense with the isolation of the intermediate of formulae Xa and Xb when preparing compounds of formula I. Thus, steps (f) and (g) may be conducted sequentially.

The first step (a) of the process of this invention wherein an azetidinone of formula II is reacted with a compound of formulae IIIa and IIIb to form the intermediate of formula IV is typically conducted in a suitable organic solvent at about room temperature. Preferably, the organic solvent is a polar organic solvent, such as dimethylformamide, but other suitable solvents such as tetrahydrofuran, acetonitrile and dimethylsulfoxide may also be used. The compound of formulae IIIa and IIIb is a diester and its hydrate form and is represented by the following formulae IIIa and IIIb

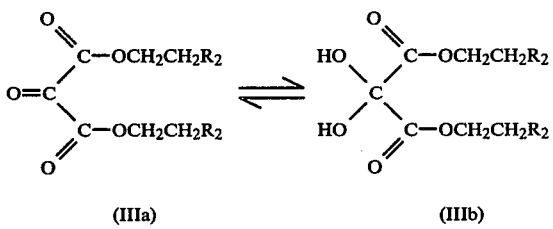

(IIIa)  (IIIb)

wherein $R_2$ is a trimethylsilyl, cyano, t-butyldiphenylsilyl or a sulfone ester of the formula $-SO_2R^1$ wherein $R^1$ is an aryl group. Other equivalently functioning (electron withdrawing) groups may also be utilized.

Preferred are the trimethylsilyl and t-butyldiphenylsilyl groups, with trimethylsilyl being most preferred due to its ready availability and ease of use.

Step (b) of the process wherein the compound of formula IV is chlorinated to form the compound of formula V is typically conducted in a suitable organic solvent at temperatures of about $-15°$ C. to $10°$ C. in the presence of an acid acceptor. Where the solvent utilized is also an acid acceptor, for instance, pyridine, no additional reagent is utilized. Alternatively, an organic solvent such as methylene chloride, chloroform or dimethyl formamide can be utilized. When this is the case, a separate acid acceptor, organic or inorganic must be added to the reaction mixture. Typical of the suitable acid acceptors are organic compounds such as pyridine or triethylamine and inorganic compounds such as sodium or potassium carbonate. As mentioned hereinabove, the chlorinating reaction may be carried out directly on the product of step (a), without isolation of the product. When this is the case, the solvent utilized is necessarily identical to that utilized in step (a). The chlorinating agent itself may be any of a variety utilized for the conversion of alcohols to chlorides such as thionyl chloride, phosphorus pentachloride, phosphorus trichloride or phosphorus oxychloride. Of these, thionyl chloride is most preferred.

Step (c) of the process wherein the chlorinated intermediate of formula V is dechlorinated and the hydroxy group of the 6-substituent concomitantly deprotected to form the intermediate of formula VI may likewise be conducted in the same solvent utilized for steps (a) and (b). However, any suitable organic solvent can be utilized, for instance, tetrahydrofuran, methylene chloride or dimethylformamide. Water, or any proton source, adjusted by the addition of a mild acid, can be added to enhance the activity of the zinc. Typical temperatures range from $-15°$ C. to about room temperature (about $25°$ C.), with a temperature of about $0°$ C. being particularly preferred. Most preferably, the removable hydroxy protecting group utilized is one which is removable by elemental zinc. However, in the event that a removable hydroxy protecting group is utilized which is not so removable (by the zinc), a separate removal step is simply conducted to remove the hydroxy protecting group. This separate removal step may occur immediately after step (c) of the instant process, or at any other time after step (c) convenient to the conduct of the process. Such removal steps are well-known in the $\beta$-lactam art.

Step (d) of the process involves the conversion of the compound of formula VI to the compound of formula VII. Typically, a polar solvent such as methanol, ethanol, dimethylformide, tetrahydrofuran or water is utilized for this reaction. Metal salts, e.g. those of silver, mercury or copper can be utilized in this step and may be any reactive salt of the metal in which the anion does not interfere in the reaction. Silver salts are preferred and include organic and inorganic salts such as silver nitrate, silver fluoborate and silver acetate, and the like with silver nitrate being most preferred. Typical suitable copper salts are those such as copper (II) acetate and copper (II) nitrate. Typical suitable mercury salts are those such as mercuric acetate. Lead salts may also be utilized although the reaction will be much slower. Silver salts are most preferred due to their ease of recovery and relative non-toxicity. The use of an acid acceptor, e.g., pyridine or triethylamine, facilitates the reaction of this step. The reaction preferably takes place under an inert atmosphere with a nitrogen atmosphere preferred.

Step (e) of the process is wherein the metal salt of formula VII is converted to the thiocarbonyl compound of formula IX by reaction of the compound of formula VII with the thiocarbonyl reagent of formula VIII. Typically, this step (e) is conducted directly upon the completion of step (d) without isolation of the metal salt intermediate of formula VII. Thus, the solvent utilized may be the same as the one used in step (d). Temperatures for the reaction of step (e) range from about 10°-45° C., with room temperature (about 25° C.) being generally preferred. The thiocarbonyl reagent of formula VIII has the following structure $$S=C(-Y)_2 \qquad \text{(VIII)}$$

wherein Y is a sulfur protecting leaving group. Typical of such leaving groups are chloro, bromo, iodo or imidazolyl. For the purposes of the process of this invention, 1,1'-thiocarbonyldiimidazole is preferred the to its crystalline nature and ease of use.

Step (f) of this process involves the removal of one protected carboxy group at position 3 of the compound of formula IX to afford the tautomer compound having formulas Xa and Xb which exist in equilibrium. The reaction of step (f) is typically conducted in a suitable organic solvent such as tetrahydrofuran, ethyl ether or dioxane at temperatures ranging from about 10°-45° C., with room temperature (about 25° C.) being preferred. Only one equivalent of fluoride ion is added so that only one of the protected carboxy groups is removed. Typically, tetrabutylammonium fluoride is utilized as a source of fluoride ion, but any equivalent source of fluoride ion may be similarly utilized. Isolation of the product at this stage affords the compound of formulas Xa and Xb which may be utilized for further synthesis of penems.

Step (g) of this process involves the reaction of the compound of formulas Xa and Xb with a compound of the formula R—Z wherein R is as hereinabove defined and Z is a leaving group, or with a compound of the formula $R_3$—CH=CH$_2$ wherein $R_3$ is hydrogen or methyl, to form a compound of formula XIII. Typically, this reaction step (g) is a continuation of step (f), and is conducted without isolation of the compound of formulas Xa and Xb. Thus, under such circumstances, the solvents utilized in steps (f) and (g) are necessarily the same. When a compound of formulas Xa and Xb is isolated, the solvents and temperatures suitable for step (g) can be different from those of step (f) but preferably are the same.

Step (h) of this process involves deprotection of the carboxy group of the compound of formula XIII to afford the antibiotic penem of formula I. The reaction conditions and reagents may be identical to those used in step (f) of the process of this invention. Preferably, tetrahydrofuran is used as the solvent, room temperature (about 25° C.), as the temperature, and tetrabutylammonium fluoride as the fluoride ion source.

The following preparations, examples, and illustrations describe in detail the processes of the present invention, methods for the preparation of the starting materials and illustrations of the use of the intermediates produced by the instant process. Throughout these preparations, examples and illustrations, "NMR" denotes nuclear magnetic resonance spectra; "rotation" denotes optical rotation of the compounds in a suitable solvent; "MS" denotes mass spectra; "UV" denotes ultaviolet spectra; and "IR" denotes infrared spectra. Chromatography is performed on silica gel unless otherwise noted. It will be apparent to those skilled in the art that many modifications, both of materials and methods, may be practiced without departing from the purpose and intent of this invention.

PREPARATION OF STARTING MATERIALS

PREPARATION A (3S, 4R)-3-(1-trichloroethoxycarbonyloxyethyl)-4-(triphenylmethylthio)azetidin-2-one To a 250 ml flask is added 7.8 grams (0.0223 m) of 3-(1-trichloroethoxycarbonyloxyethyl)-4-acetoxyazatadimo-2-one, 220 ml acetonitrile, 2.6 grams (0.252 m) cesium carbonate, and 5.2 grams (0.0188 m) triphenylmethanethiol (tritylthiol). After stirring for 5 hours, and additional 1.0 gram (0.0036 m) triphenylmethanethiol is added and the mixture is stirred for another one-half hour. After overnight refrigeration, the solids are removed by filtration and the solvents by evaporation under vacuum. The crude reaction product is chromatographed on coarse silica gel eluting with methylene chloride changing to 10% and 20% ethyl acetate/methylene chloride to afford 7.89 grams (3S,4R)-3-(1-trichloroethoxycarbonyloxyethyl)-4-(triphenylmethlthio)azetidin-2-one with spectra as follows:

NMR: =7.7–7.1,16H; 5.05,1H,m; 4.85,2H,q (J=18 Hz); 4.45,1H,d(J=1.5 Hz); 3.3, 1H,dd(J=1.5,9 Hz); 1.5,3H,d(J=9 Hz).

PREPARATION B

DI(TRIMETHYLSILYLETHYL)KETOMALONATE (a) In 100 ml of methylene chloride is dissolved 22.50 grams 2-trimethylsilylethanol. To this is added 20.00 grams triethylamine. After cooling to about −20° C., a solution of 15 grams of freshly distilled malonyl dichloride in 100 ml methylene chloride is added slowly over a period of one and one-half hours. After the addition is completed, the reaction mixture is allowed to warm to room temperature and then is washed twice with 500 ml portions of water, followed by washings with 5% sodium bicarbonate solution until the pH is greater than 9. The solution is then dried over anhydrous magnesium sulfate and the solvents removed by evaporation to yield 30.22 grams of the product, the trimethylsilyl diester of malonic acid.

(b) The diester prepared as described in paragraph (c) herein is dissolved in 300 ml benzene. To this solution is added 140 mg benzoic acid, 17 ml benzaldehyde and sufficient piperidine to afford a pH of about 9. The solution is refluxed with a Dean-Stark tube for 8 hours and then the solvents are removed under vacuum to afford, as the product, di(-trimethylsilylethyl)benzlidinemalonate.

(c) The benzylidene malonate prepared as described in paragraph (b) herein is dissolved in 500 ml methylene chloride and cooled to about −78° C. Ozone is then bubbled into the solution until a distinct blue to blue-green color persists. The ozone is then discontinued and the solution is allowed to stand for five to ten minutes. Nitrogen is then passed into the reaction vessel until the excess ozone is completely removed. 75 milliliters of dimethyl sulfide is added and the reaction mixture is allowed to come to room temperature. The solution is then evaporated to dryness and the resulting oil is placed in an open dish to allow any excess benzaldehyde to oxidize. After standing overnight, the semicrystalline mass is dissolved in methylene chloride and washed, first with saturated sodium bicarbonate solution, and then with water. The washed methylene chloride solution is dried over anhydrous magnesium sulfate and the solvents removed. The resulting oil/crystalline mass is recrystallized from petroleum ether to afford di(trimethylsilylethyl)ketomalonate.

DESCRIPTION OF THE PROCESS STEPS OF THIS INVENTION

EXAMPLE 1

(5R,6S,8R)-2-ETHYLTHIO-6-(1 HYDROXYETHYL) PENEM-3-CARBOXYLIC ACID

A. 30.0 grams (3S,4R)-3-[1-(2,2,2-trichloroethoxycarbonyloxyethyl)]-4-(triphenylmethylthio)azetidin-2-one (prepared as described in Preparation A) is dissolved in 6 ml dimethylformamide. To this solution is added 2.0 grams di(trimethylsilylethyl) ketomalonate (prepared as described in Preparation B) and molecular sieves. After standing for two days at room temperature, the reaction mixture is partitioned between water and methylene chloride. The organic layer is separated and the solvents removed by a rotary evaporation. The crude reaction product is purified by column chromatography on silica gel eluting with methylene chloride changing to 2% ethyl acetate/methylene chloride to yield 4.26 grams (3S,4R)-1-[1-hydroxy-1,1-di(trimethylsilylethoxycarbonyl)methyl]-3-[1-(2,2,2-trichloroethoxycarbonyloxyethyl)]-4-triphenylmethlthio)azetidin-2-one, having spectra as follows:

NMR: $\delta$=7.5–7.1,15H; 5.05,1H,m; 4.65,2H, s; 4.5,1H,d(J=1.5 Hz); 4.2,4H,m; 3.45,1H,dd(J=1.5,7 Hz); 1.05,3H,d (J=7 Hz); 0.9,4H,m; 0.05,18H.

B. To a solution of 10 ml methylene chloride, 2 ml pyridine and 1.0 gram calcium carbonate is added 4.26 gram (3S,4R)-1-[1-hydroxy-1,1-di(trimethylsilylethoxycarbonyl)methyl]-3-[1-(2,2,2-trichloroethoxycarbonyloxyethyl)]-4-triphenylmethylthio)azetidin-2-one. After placing the mixture in an ice bath, 1.5 ml of thionyl chloride is slowly added. After one-half hour, the reaction is complete. The reaction mixture is then washed with sodium bicarbonate solution of pH less than 8 and the solvent removed under vacuum. Chromatography on silica gel using methylene chloride as eluant affords 3.48 grams of the product, (3S,4R)-1-[1-chloro-1,1-di(trimethylsilylethoxycarbonyl)methyl]-3-[1-(2,2,2-trichloroethoxycarbonyloxylthyl]-4-(triphenylmethylthio)azetidin-2-one.

C. 3.48 grams of (3S,4R)-1-[1-chloro-1,1-di(trimethylsilylethoxycarbonyl)methyl]-3-[1-(2,2,2-trichloroethoxycarbonyloxyethyl]-4-triphenylmethylthio)azetidin-2-one is dissolved in 50 ml tetrahydrofuran. To this solution is added 15 ml water and 8 grams zinc dust. The mixture is then placed in an ice bath and 16 grams of ammonium chloride is added in portions over a period of one hour. After a period of two hours, 4 ml of 100% acetic acid is added, and then, portionwise, an additional 6 grams of zinc dust. After a further period of one hour, the reaction mixture is filtered, and the solvents removed under vacuum. The crude product is partitioned between water and methylene chloride. Purification by column chromatography on silica gel using as eluant, 1% ethyl acetate/methylene chloride changing to 25% ethyl acetate/methylene chloride affords 1.644 grams of the desired product, (3S,4R)-1-[1,1-di(trimethylsilylethoxycarbonyl)methyl]-3-(1-hydroxyethyl)-4-(triphenylmethylthio)azetidin-2-one, having spectra as follows:

NMR: =7.5–7,15H; 4.15,5H; 3.9,1H,s; 3.4,1H,dd(J=1.5,6 Hz); 1.05,3H,d (J=6 Hz); 0.95,4H,m; 0.5,18H.

D. To a 25 ml flask equipped with a nitrogen atmosphere is added 1 ml methanol and 200 mg (0.000289 moles) (3S,4R)-1-[1,1-di(trimethylsilylethoxycarbonyl)methyl]-3-(1-hydroxyethyl)-4-(triphenylmethylthio)azetidin-2-one. The solution is cooled about 0° C. and 0.025 ml (25 mg, 0.000317 moles) pyridine and 54 mg (0.000317 mates) silver nitrate in 1 ml methanol are added. The mixture is allowed to warm to room temperature, with stirring. After two hours, the methanol is removed under high vacuum to afford silver (3S,4R)-3-(1-hydroxyethyl)1-di($\beta$-trimethylsilylethyl-2-malonate)]-azetidin-2-one-4-thiolate.

E. Silver (3S,4R)-3-(1-hydroxyethyl)-1-di($\beta$-trimethylsilylethyl-2-malonate)]-azetidin-2-one-4-thiolate is dissolved in 2 ml methylene chloride and to this solution is added 68 mg (0.000346 moles) 1,1'-thiocarbonyldiimidazole. After stirring another hour, an additional 60 mg of 1,1'-thiocarbonyldiimidazole is added. Stirring is continued for another 1.5 hour, at which time, the reaction mixture is applied directly to a chromatography column of silica gel. Elution with methylene chloride affords the desired product, (5R,6S,8R)-2-thiocarbonyl-3,3-di(trimethylsilylethoxy-carbonyl)-6-(1-hydroxyethyl)penam, having spectra as follows:

NMR: =5.7,1H,d(J=1 Hz); 4.2,5H,m; 3.65, 1H,dd(J=1,8 Hz); 1.3,3H,d(J=8 Hz); 0.95,4H,m; 0.05,18H.

F. 61 miligrams of (5R,6S,8R)-2-thiocarbonyl-3,3-di(-trimethylsilylethoxycarbonyl)-6-(1-hydroxyethyl)penam is dissolved in 5 ml tetrahydrofuran and 2 equivalents of tetrabutylammonium fluoride in 10 ml tetrahydrofuran is slowly added at room temperature. Thin layer chromatography (silica, 10% ethyl acetate/methylene chloride) showed the immediate presence of the monodeprotected decarboxylated compound (5R,6S,8R)-2-thiocarbonyl-3-(trimethylsilylethoxycarbonyl)-6-(1-hydroxyethyl)penam, which exists in equilibrium with (5R,6S,8R)-2-thiol-3-(trimethylsilylethoxycarbonyl)-6-(1-hydroxyethyl)penem as follows

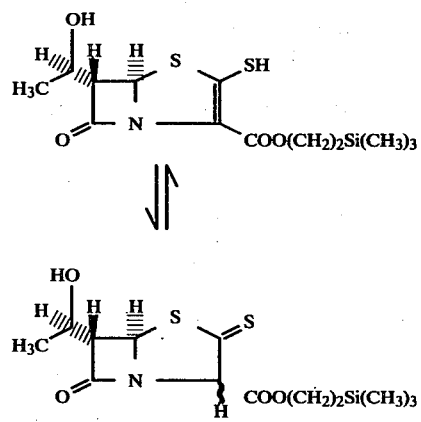

G. To the solution of (5R,6S,8R)-2-thiocarbonyl-3-(trimethylsilylethoxycarbonyl)-6-(1-hydroxyethyl)penam and (5R,6S,8R)-2-thiol-3-(trimethylsilylethoxycarbonyl)-6-(1-hydroxyethyl) penem produced in the above step F is added 2 ml of ethyl iodide. The reaction mixture is then partitioned between water and ethyl acetate. The organic layer is separated, and the solvents are removed by rotary evaporation to yield the desired product, (5R,6S,8R)-$\beta$-(trimethylsilyl)ethyl-2-ethylthio-6-(1-hydroxyethyl)penem-3-carboxylate, having spectra as follows:

NMR: =5.7,1H,d(J=1.5 Hz); 4.2,5H,m; 3.7,1H,dd(J=1.5,7 Hz); 3,2H,m; 1.4–0.9,8H; 0.05,9H.

H. 40 miligrams of (5R,6S,8R)-$\beta$-(trimethylsilyl)ethyl-2-ethylthio-6-(1-hydroxyethyl)penem-3-carboxylate is dissolved in 1 ml tetrahydrofuran and to this is slowly added one equivalent of tetrabutylammonium fluoride in 2 ml tetrahydrofuran at room temperature. After 15 minutes, the reaction is complete as shown by thin layer chromatography. Acidification with phosphoric acid to a pH not below 2, followed by purification affords the desired product, (5R,6S,8R)-2-ethylthio-6-(1-hydroxyethyl)penem-3-carboxylic acid, identifiable by spectra and bioautogram with authentic (5R,6S,8R)-2-ethylthio-6-(1-hydroxyethyl)penem-3-carboxylic acid.

EXAMPLE 2

Repetition of the procedures detailed in Example 1, steps a thru h, except substituting methyl iodide for the ethyl iodide utilized in step g, affords (5R,6S,8R)-2-methylthio-6-(1-hydroxyethyl)penem-3-carboxylic acid.

EXAMPLE 3

Substantial repetition of the procedures detailed in Example 1 utilizing n-propyliodide in place of the ethyl iodide of step g yields (5R,6S,8R)-2-n-propylthio-6-(1-hydroxyethyl)penem-3-carboxylic acid.

EXAMPLE 4

Using the identical materials except for the substitution of isoprophyl iodide for the ethyl iodide of step g and repetition of the procedures detailed in Example 1 affords (5R,6S,8R)-2-isopropylthio-6-(1-hydroxyethyl)-penem-3-carboxylic acid.

EXAMPLE 5

Following the procedures detailed in Example 1 but utilizing ethylene and a radical initiator known in the art, such as AIBN[2,2'-azobis(2-methylpropionitrile)] in step g in place of the ethyl iodide, there is afforded (5R,6S,8R)-2-ethylthio-6-(1-hydroxyethyl)penem-3-carboxylic acid.

What is claimed is:

1. A process for the production of penems of the formula I:

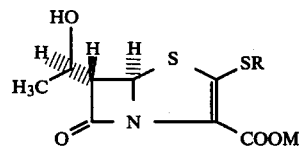

wherein R is methyl, ethyl, propyl, or isopropyl; and M is an alkali metal cation;
which comprises:
(a) reaction of an azetidinone of the formula II

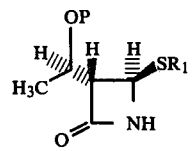

wherein P is a removable hydroxy protecting group; and
$R_1$ is a sulfur protecting group selected from triphenylmethyl, 2-pyranyl, or lower alkyl carbonyl;
with a compound of the formulae IIIa and IIIb

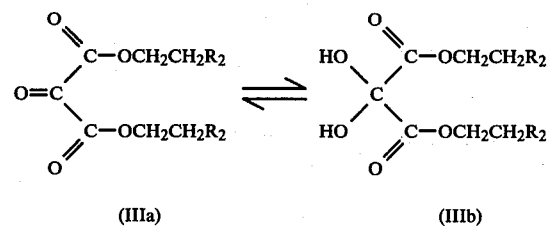

wherein $R_2$ is a trimethylsilyl, cyano, t-butyl diphenylsilyl or a sulfone ester of the formula —$SO_2R^1$ wherein $R^1$ is an aryl; to form the intermediate of the formula IV

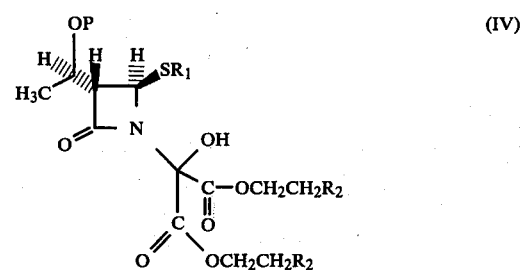

wherein R, $R_1$ and $R_2$ are as hereinabove defined;
(b) treatment of the compound of formula IV with a chlorinating agent to form a compound of the formula V

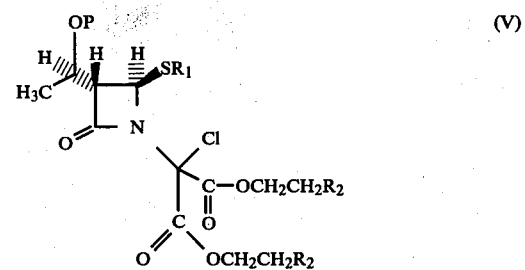

wherein P, $R_1$ and $R_2$ are as hereinabove defined;
(c) treatment of the compound of formula V with elemental zinc to effect removal of the chlorine and the removable hydroxy protecting group, and, if a removable hydroxy protecting group is utilized which is not removable with zinc, subsequent removal of said hydroxy protecting group, producing a compound of the formula VI

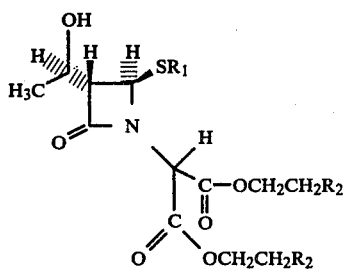
(VI)

where $R_1$ and $R_2$ are as hereinabove defined;

(d) treatment of the compound of formula VI with a reactive silver, copper or mercury salt to form a compound of the formula VII

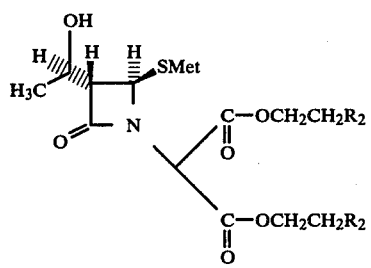
(VII)

wherein $R_2$ is hereinabove defined and Met is silver, copper or mercury;

(e) reaction of the intermediate of formula VII with a thiocarbonyl compound of the formula VIII

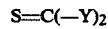 (VIII)

wherein Y is a leaving group;

to form a compound of the formula IX

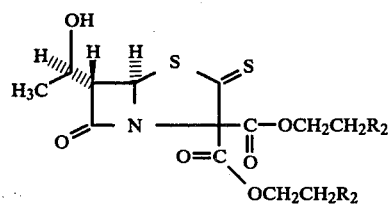
(IX)

wherein $R_2$ is as hereinabove defined;

(f) treatment of the compound of formula IX with one equivalent of fluoride ion to form the compound of the formulae Xa and Xb

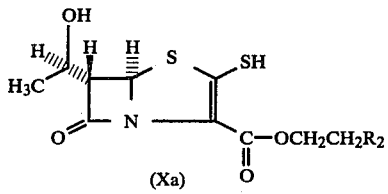
(Xa)

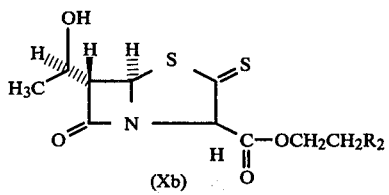
(Xb)

wherein $R_2$ is as hereinabove defined;

(g) reaction of the compound of formulas Xa and Xb with either a compound of formula XI

 (XI)

wherein R is as hereinabove defined and Z is a leaving group, to make compounds of formula I wherein R is methyl, ethyl, propyl or isopropyl; or a compound of the formula XII

 (XII)

wherein $R_3$ is hydrogen or methyl, to make compounds of formula I wherein R is ethyl, propyl or isopropyl; forming a compound of the formula XIII

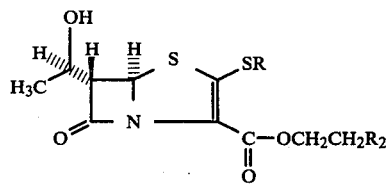
(XIII)

wherein R is methyl, ethyl, propyl or isopropyl and $R_2$ are as hereinabove defined; and (h) treatment of a compound of formula XIII with another equivalent of fluoride ion to form a compound of formula I.

2. A process according to claim 1 wherein the compounds of formulas IV and V are utilized without isolation in the process step immediately succeeding the process step.

3. A process according to claim 1 wherein the compounds of formula VII are utilized without isolation in the process step immediately succeeding the process step in which they are formed.

4. A process according to claim 1 wherein the compound of formulas Xa and Xb is utilized without isolation in the process step immediately succeeding the process step in which they are formed.

5. A process according to claim 1 wherein the compound of formulas IV, V, VII Xa and Xb are each utilized without isolation in the process step immediately succeeding the process step in which each is formed.

6. A process for the preparation a penem compound of the formulae Xa and Xb

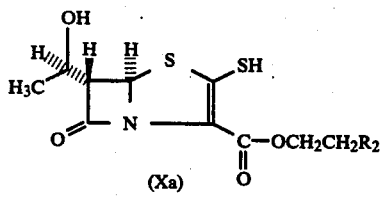
(Xa)

⇌

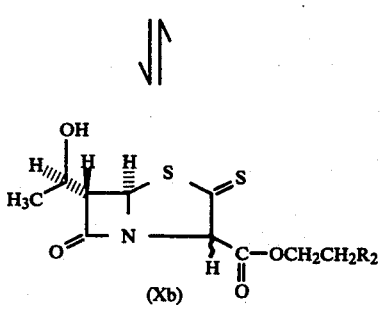
(Xb)

wherein $R_2$ is trimethylsilyl, cyano, t-butyldiphenylsilyl or a sulfone of the formula $-SO_2R^1$ where in $R^1$ is aryl which comprises (a) reaction of an azetidinone of the formula II

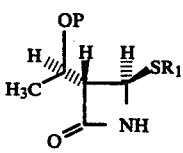
(II)

wherein P is a removable hydroxy protecting group; and $R_1$ is a sulfur protecting group selected from triphenylmethyl, 2-pyranyl or lower alkyl carbonyl; with a compound of the formulae IIIa and IIIb

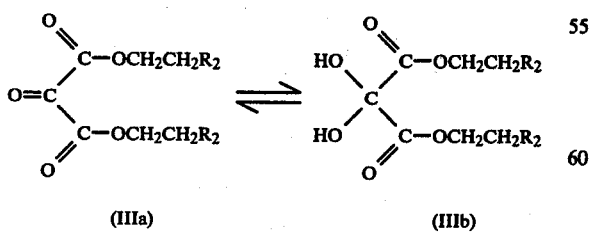
(IIIa) (IIIb)

wherein $R_2$ is trimethylsilyl, cyano, t-butyldi phenylsilyl, or a sulfone of the formula $-SO_2R^1$ wherein $R^1$ is aryl; to form a compound of the formula IV

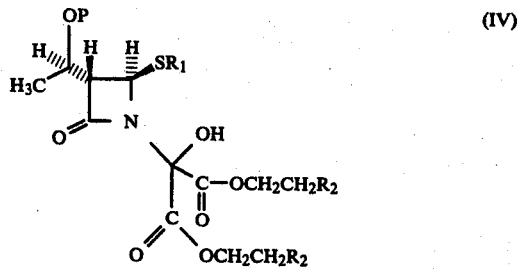
(IV)

wherein P, $R_1$ and $R_2$ are as hereinabove defined;

(b) treatment of the compound of formula IV with a chlorinating agent to form the compound of the formula V

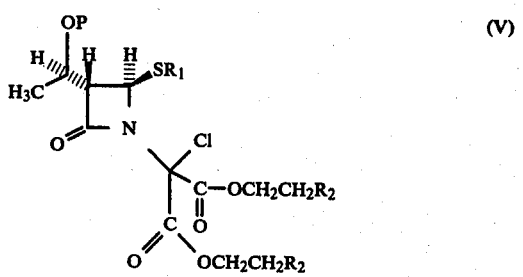
(V)

wherein P, $R_1$ and $R_2$ are as hereinabove defined;

(c) treatment of the compound of formula V with elemental zinc to effect removal of the chlorine and the hydroxy protecting group, and, if a removable hydroxy protecting group is utilized which is not removable with zinc, subsequent removal of said hydroxy protecting group, producing a compound of the formula VI

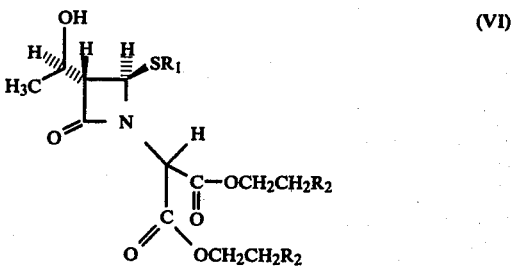
(VI)

wherein $R_1$ and $R_2$ are as hereinabove defined;

(d) treatment of a compound of formula VI with a reactive silver, copper or mercury salt to form a compound of the formula VII

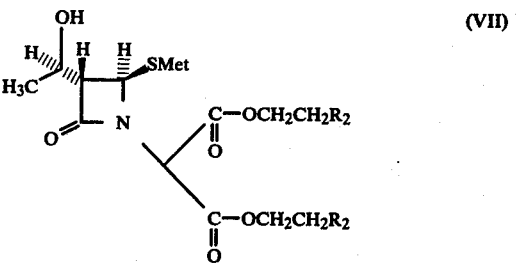
(VII)

wherein $R_2$ is as hereinabove defined and Met is silver, copper or mercury;

(e) reaction of the compound of formula VII with a thiocarbonyl compound of the formula VIII $$S=C(-Y)_2 \quad (VIII)$$

wherein Y is a leaving group; to form a compound of the formula IX

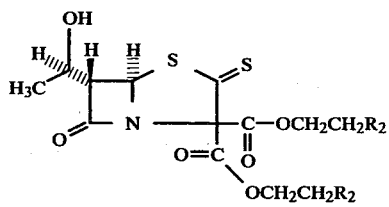

wherein $R_2$ is as hereinabove defined; and (f) treatment of a compound of formula IX with one equivalent of fluoride ion to form the penem intermediate of formulas Xa and Xb.

7. A process according to claim 6 wherein the compounds of formulas IV and V are each utilized without isolation in the process step immediately succeeding the process steps in which each is formed.

8. A process according to claim 6 wherein a compound of formula VII is utilized without isolation in the process step immediately succeeding the process step in which it is formed.

9. A process according to claim 1 or 6 wherein P is a trichloroethoxycarbonyl group.

10. A process according to claim 1 or 6 wherein $R_1$ is a triphenylmethyl group.

11. A process according to claim 1 or 6 wherein $R_2$ is a trimethylsilyl group.

12. A process according to claim 1 or 6 wherein thionyl chloride is utilized as the chlorinating agent.

13. A process according to claim 1 or 6 wherein a reactive silver salt is utilized to form a compound of formula IX.

14. A process according to claim 13 wherein the reactive silver salt utilized is silver nitrate.

15. A process according to claim 1 or 6 wherein the thiocarbonyl compound of formula X utilized is 1,1-thiocarbonyldiimidazole.

16. A process according to claim 1 or 6 wherein the fluoride ion is utilized in the form of tetrabutylammonium fluoride.

* * * * *